United States Patent
Dakshanamurthy et al.

(10) Patent No.: US 11,373,734 B2
(45) Date of Patent: Jun. 28, 2022

(54) METHODS AND SYSTEMS FOR POPULATING AND SEARCHING A DRUG INFORMATICS DATABASE

(71) Applicant: Georgetown University, Washington, DC (US)

(72) Inventors: Sivanesan Dakshanamurthy, Herndon, VA (US); Oakland John Peter, District Heights, MD (US)

(73) Assignee: Georgetown University, Washington, DC (US)

( * ) Notice: Subject to any disclaimer, the term of this patent is extended or adjusted under 35 U.S.C. 154(b) by 0 days.

(21) Appl. No.: 14/401,633

(22) PCT Filed: May 20, 2013

(86) PCT No.: PCT/US2013/041807
§ 371 (c)(1),
(2) Date: Nov. 17, 2014

(87) PCT Pub. No.: WO2013/173826
PCT Pub. Date: Nov. 21, 2013

(65) Prior Publication Data
US 2015/0142730 A1 May 21, 2015

Related U.S. Application Data

(60) Provisional application No. 61/648,908, filed on May 18, 2012.

(51) Int. Cl.
*G06F 16/00* (2019.01)
*G16B 50/00* (2019.01)
(Continued)

(52) U.S. Cl.
CPC ............ *G16B 50/00* (2019.02); *G06F 16/21* (2019.01); *G06F 16/248* (2019.01); *G16B 50/20* (2019.02);
(Continued)

(58) Field of Classification Search
None
See application file for complete search history.

(56) References Cited

U.S. PATENT DOCUMENTS 5,577,239 A * 11/1996 Moore ................... G16C 20/90
707/752
7,133,868 B1 * 11/2006 Ruest ................ G06F 17/30893
(Continued)

FOREIGN PATENT DOCUMENTS

EP 2444914 A2 4/2012

OTHER PUBLICATIONS

Campagna-Slater et al. (Pharmacophore Screening of the Protein Data Bank for Specific Binding Site Chemistry. J. Chem. Model. Jan. 29, 2010.*
(Continued)

*Primary Examiner* — Tuankhanh D Phan
(74) *Attorney, Agent, or Firm* — Blank Rome LLP

(57) ABSTRACT

The present invention provides a method for populating and searching a drug informatics database that includes receiving unprocessed data associated with a chemical compound from one or more data sources. The unprocessed data is parsed into a plurality of data objects based on a categorization associated with each of the data objects. Additional information, such as explanatory notes, is identified and associated with at least one of the data objects. The data objects are stored in entries within a data structure, where the data structure is searchable based on one or more of the data objects. A query for data associated with a chemical
(Continued)

compound is received at a drug informatics database. The drug informatics database is then searched for data associated with the chemical compound and the search results are provided to a user.

15 Claims, 4 Drawing Sheets

(51) Int. Cl.
  *G06F 16/248* (2019.01)
  *G06F 16/21* (2019.01)
  *G16H 70/40* (2018.01)
  *G16B 50/20* (2019.01)
  *H04L 67/10* (2022.01)
  *G16B 45/00* (2019.01)

(52) U.S. Cl.
  CPC .............. *G16H 70/40* (2018.01); *H04L 67/10* (2013.01); *G16B 45/00* (2019.02)

(56) References Cited

U.S. PATENT DOCUMENTS

| | | | |
|---|---|---|---|
| 7,620,565 B2 | 11/2009 | Abelow | |
| 7,752,191 B2 | 7/2010 | Kehl | |
| 7,930,262 B2 | 4/2011 | Friedlander et al. | |
| 8,108,384 B2* | 1/2012 | Sanchez | G06F 19/28 707/722 |
| 8,148,503 B2 | 4/2012 | Litosh et al. | |
| 2004/0006559 A1* | 1/2004 | Gange | G06F 16/24578 |
| 2004/0093331 A1* | 5/2004 | Garner | A61P 25/06 |
| 2007/0061084 A1* | 3/2007 | Farnet | C12Q 1/02 702/19 |
| 2008/0033999 A1 | 2/2008 | Gardner | |
| 2010/0250497 A1* | 9/2010 | Redlich | F41H 13/00 707/661 |
| 2010/0312538 A1* | 12/2010 | Umeyama | C40B 30/02 703/12 |
| 2011/0301193 A1* | 12/2011 | Errico | C07D 401/12 514/314 |
| 2012/0084299 A1* | 4/2012 | Cai | G16C 20/40 707/E17.084 |

OTHER PUBLICATIONS

Forsythe Ian et al. (Exploring Human Metabolites Using the Human Metabolome Database). Mar. 2009.*

Schomburg et al., "From structure siagrams to visual chemical pattern," J. Chem. Inf. Model, 2010, vol. 50, pp. 1529-1535.

* cited by examiner

METHODS AND SYSTEMS FOR POPULATING AND SEARCHING A DRUG INFORMATICS DATABASE

REFERENCE TO RELATED APPLICATION

The present application claims the benefit of U.S. Provisional Patent Application No. 61/648,908, filed May 18, 2012, whose disclosure is hereby incorporated by reference in its entirety into the present disclosure.

FIELD OF THE INVENTION

The present invention relates to databases. More specifically, the present invention relates to populating and searching a drug informatics database.

BACKGROUND OF THE INVENTION

Cheminformatics is the study of the use of databases in handling chemical knowledge. Cheminformatics focuses on a wide range of small molecules and serves a critical role in the development of new materials and pharmaceuticals by aiding in the selection of starting points for experimental development. Drug informatics is the application of cheminformatics specifically to drugs and pharmaceutical compounds.

The Chemical Abstracts Service (CAS) is searchable web-based database for chemical information. The CAS database is curated and quality-controlled by human operators. The CAS database contains a wide variety of substances, including organic compounds, inorganic compounds, metals, alloys, minerals, coordination compounds, organometallics, elements, isotopes, nuclear particles, proteins and nucleic acids, polymers, and nonstructurable materials. Chemical compounds in the CAS database can be described in many different ways, including molecular formula, structure diagram, systematic names, generic names, proprietary or trade names, and trivial names.

Therefore, the CAS database is also indexed by CAS registry numbers, which are unique identifiers for chemical substances. A CAS registry number is a numeric identifier that can contain up to ten digits, divided by hyphens into three parts, where the right-most digit is a check digit used to verify the validity and uniqueness of the entire number. Properties of CAS registry numbers include that is a unique numeric identifier, it designates only one substance, it has no chemical significance, and it links to additional information about a specific chemical substance. Thus, while a CAS registry number itself has no inherent chemical significance, it provides a way to identify a chemical substance or molecular structure when there are many possible systematic, generic, proprietary, or trivial names.

Another example of a structure/substructure search engine for a chemical compound database includes the PubChem, ChemSpider, and eMolecule databases, which are each based on traditional relational database engines that is required because of the large volume of data involved. Intimately related to the development of the representation of molecular properties is the ability to compare molecules and extract which ones are most similar in some sense. The search for structural fragments (e.g., substructures) of a compound is very important in medicinal chemistry, QSAR, spectroscopy, and many other fields.

One problem associated with conventional cheminformatics and drug information databases is that chemical structure data may not map directly into the data types that conventional database engines are designed to handle.

Thus, there is a need for populating and searching a drug informatics database that include efficient representation, populating, and searching of the chemical and physical properties as well as the structures of molecules.

SUMMARY OF THE INVENTION

In order to overcome the disadvantages of the prior art, the subject matter described herein includes a method for populating a drug informatics database that includes receiving unprocessed data associated with a chemical compound from one or more data sources. The unprocessed data is parsed into a plurality of data objects based on a categorization associated with each of the data objects. Additional information, such as explanatory notes, is identified and associated with at least one of the data objects. The data objects are stored in entries within a data structure, where the data structure is searchable based on one or more of the data objects.

The subject matter described herein further includes a method for searching a drug informatics database that includes receiving, at a drug informatics database, a query for data associated with a chemical compound. The drug informatics database is searched for data associated with the chemical compound and the search results are provided to a user.

A drug informatics database includes a primary data structure and a auxiliary data structure. The primary data structure is configured for storing primary data objects in entries, where the data structure is searchable based on one or more of the data object associated with one or more chemical compounds. The auxiliary data structure is configured for storing auxiliary data objects in entries associated with the one or more chemical compounds, where the auxiliary data objects are linked to the primary data objects.

Other objects, advantages and salient features of the invention will become apparent from the following detailed description, which, taken in conjunction with the annexed drawings, discloses a preferred embodiment of the present invention.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying Figures.

DETAILED DESCRIPTION OF THE INVENTION

Figure 1:
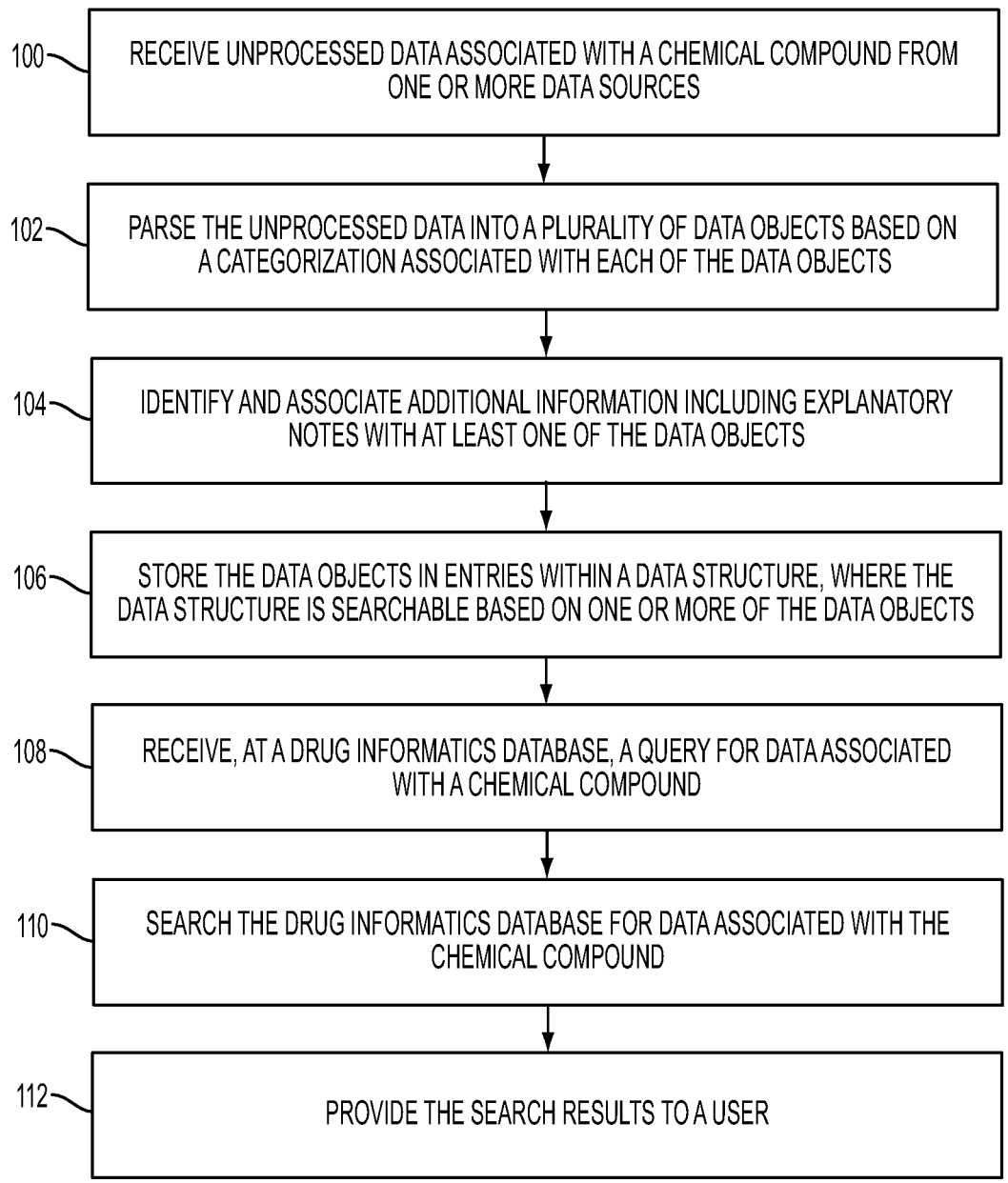
FIG. 1 is a flow chart showing exemplary steps for populating and searching a drug informatics database according to an embodiment of the subject matter described herein.

The present invention will be described in terms of one or more examples, with reference to the accompanying drawings. In the drawings, like reference numbers indicate identical or functionally similar elements. Additionally, the leftmost digit(s) of most reference numbers may identify the drawing in which the reference numbers first appear.

The present invention will be explained in terms of exemplary embodiments. This specification discloses one or more embodiments that incorporate the features of this invention. The disclosure herein will provide examples of embodiments, including examples of data analysis from which those skilled in the art will appreciate various novel approaches and features developed by the inventors. These various novel approaches and features, as they may appear herein, may be used individually, or in combination with each other as desired.

In particular, the embodiment(s) described, and references in the specification to "one embodiment", "an embodiment", "an example embodiment", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, persons skilled in the art may effect such feature, structure, or characteristic in connection with other embodiments whether or not explicitly described.

Embodiments of the invention may be implemented in hardware, firmware, software, or any combination thereof, or may be implemented without automated computing equipment. Embodiments of the invention may also be implemented as instructions stored on a machine-readable medium, which may be read and executed by one or more processors. A machine-readable medium may include any mechanism for storing or transmitting information in a form readable by a machine (e.g. a computing device). For example, a machine-readable medium may include read only memory (ROM); random access memory (RAM); hardware memory in PDAs, mobile telephones, and other portable devices; magnetic disk storage media; optical storage media; flash memory devices; electrical, optical, acoustical, or other forms of propagated signals (e.g. carrier waves, infrared signals, digital signals, analog signals, etc.), and others. Further, firmware, software, routines, instructions, may be described herein as performing certain actions. However, it should be appreciated that such descriptions are merely for convenience and that such actions in fact result from computing devices, processors, controllers or other devices executing the firmware, software, routines, instructions, etc.

FIG. 1 is a flow chart showing exemplary steps for populating and searching a drug informatics database according to an embodiment of the subject matter described herein. Referring to FIG. 1, at step 100, unprocessed data associated with a chemical compound is received from one or more data sources. For example, unprocessed data may be received from one of chemical companies, public databases, and public literature.

At step 102, the unprocessed data is parsed into a plurality of data objects based on a categorization associated with each of the data objects. The unprocessed data is gathered, or immediately converted, into structure-data files (SDF) files, having the format .sdf, which is an extension of MDL Molefiles produced by Molecular Design Limited, Inc., which is part of Symyx Technologies, which is part of Accelrys, headquartered in San Diego, Calif. The SDF files go through several steps in order to be suitable for substructure searching. For example, parsing the unprocessed data may include identifying one of a company name, a company drug id, a molecular weight, and bibliographic information associated with a chemical compound.

In one embodiment, an SDF file representing a 2D/3D structural format in terms of Cartesian co-ordinates is processed to yield MySQL tabular information. First, a program such as Molconvert produced by the ChemAxon Corporation is applied to the SDF file to yield a file consisting of simplified molecular-input line-entry system (SMILES) strings for all compounds. This Molconvert function creates a text file based on an SDF, which contains one SMILES string per molecule in the original SDF file. Second, because there are multiple possible SMILES strings possible for any given single chemical compound, another ChemAxon utility called Standardizer is employed to rewrite each SMILES in a unique 'canonical' form. Third, a Perl script is used to interleave the standardized SMILES into the original SDF file. Thus, these SMILES are placed into the SDF file, where each SMILES is paired with its Molefile record. Fourth, another Perl script is used to reformat this SMILES-bearing SDF file into a field-and record-delimited flat file. These flat files consist of the Molefile record, molecular weight, company name (or name of data source), and a company/datasource id number, and all other data fields in the SDF file are discarded. Finally, this flat-file is incorporated into MySQL via, for example, a 'LOAD DATA INFILE' statement, which may be significantly faster than conventional data loading.

At step 104, additional information is identified and associated with at least one of the data objects. In one embodiment, one or more SMILES string(s) may be automatically generated for the chemical compound. SMILES is a specification in the form of a line notation for describing the structure of chemical molecules using short ASCII strings. SMILES strings can be imported by most molecule editors for conversion back into two-dimensional drawings or three-dimensional models of the molecules. It is appreciated that while the term SMILES typically refers to a line notation for encoding molecular structures and specific instances, SMILES is also commonly used to refer to both a single SMILES string and a number of SMILES strings. Therefore, both usages of a SMILES string may be used without departing from the scope of the subject matter described herein and the exact meaning of the term may be apparent from the context to one of ordinary skill in the art. In terms of a graph-based computational procedure, SMILES is a string obtained by printing the symbol nodes encountered in a depth-first tree traversal of a chemical graph. In order to generate a SMILES string, the chemical graph is first trimmed to remove hydrogen atoms and cycles are broken to turn it into a spanning tree. Where cycles have been broken, numeric suffix labels are included to indicate the connected nodes and parentheses are used to indicate points of branching on the tree.

At step 106, the data objects are stored in entries within a data structure, where the data structure is searchable based on one or more of the data objects. For example, storing the data objects may include standardizing the data objects by associating a single unique representation with each of the chemical compounds. Additionally, standardizing the data may include replacing, for example, aromatic systems with aromatic bonds and replacing explicit atoms with implicit atoms.

At step 108, a query for data associated with a chemical compound is received at a drug informatics database. For example, the query may include a visual representation of the chemical compound. Using a script such as 'index.php', the user starts a PHP session. This session is identified by a session id which will be used to name files and MySQL tables unique to this user. The user draws a query molecule into a MarvinSketch applet, where this applet converts the drawn compound into a SMILES string, which will be passed to write_smiles_file.php via a URL query after a search button is pressed. The user chooses data columns and number of results per page to be returned by the search. This information is written to a cookie variable, and is retrieved and used by insert_into_screening.php to form a MySQL command. The user then launches a search by pressing one of the search buttons (e.g., 'Substructure, or 'Screening' search types), where the type of search is written to a cookie variable. Upon pressing one of these buttons, operation is passed to 'write_smiles_file.php'.

At step 110, the drug informatics database is searched for data associated with the chemical compound. For example, searching the drug informatics database may include converting the visual representation of the chemical compound described in step 108 into a search string that is understandable by the database. Searching the drug informatics database may also include using one of structure-based searching, property-based searching, similarity-based searching, or matching similarity over existing experimentally validated compounds.

In one embodiment, searching the drug informatics database may include performing a substructure search on a subset of the drug informatics database and incrementally caching the search results in real time or near real time. To begin a search, a user draws a chemical compound (the query) into a MarvinView applet, which is defined via the mview.js Javascript library, provided as a part of MarvinBeans produced by the ChemAxon Corporation. For example, using a php script called 'write_smiles_file.php', the server receives the SMILES string via a URL parameter that was originally written by 'index.php'. Write_smiles_file.php writes the SMILES to a text file named query_PHPSESSIONID.smiles, where PHPSESSIONID is the php session id for this user, and then passes operation to another php script called 'call_jcman.php'.

In 'call_jcman.php', the server deletes and then creates, or recreates, the query table via the function "remove_and_create_table('$table')." The function 'remove_and_create_table($table)' is a PHP function, rather than a PHP script. and checks to see if $table exists in the MySQL database. If so, the function deletes the $table. Next, remove_and_create_table($table) uses 'jcman' to create/recreate the $table. Returning to call_jcman.php, call_jcman.php uses 'jcman' to write the query file into the query table, updates the query table to remove newlines from the SMILES field, and passes operation to another php script called 'insert_into_screening'

When 'insert_into_screening.php' is executed, the server deletes and recreates the screening table via remove_and_create_table('screening table') function as described above with respect to $table. Insert_into_screening.php' then deletes and recreates the jcsearch table via the remove_and_create_table('jcsearch table') function in a manner similar to that described above with respect to $table, and deletes the jcsearch file. Next, 'insert_into_screening.php' starts the process of adding search results to the jcsearch table by calling the function 'gather_more_results( )'. The 'gather_more_results( )' PHP function acts as a method for calling 'cmdline_insert_into_screening.php' without making the user's browser wait for that function so that the user can continue browsing while data is being processed. Returning to 'insert_into_screening.php', 'insert_into_screening.php' forms the MySQL select command used to display results, using column information specified by cookies. Next, this MySQL select command is written to a text 'pipe' file named based on the PHP session id. This data is then passed, in file format, in order to reduce the opportunity for a malicious MySQL injection attack.

Thus, it may be appreciated from the exemplary steps described above, that in order to allow the entire database to be searched incrementally, which may include approximately 35 million compounds, subsets or portions of the database may be searched sequentially. For example, 1,000 to 10,000 compounds, depending on settings, are placed into a screening table and then subjected to a substructure search via the jcsearch function, which is part of ChemAxon's JChem Web Services package. Compounds from the screening table that contain the query compound are then placed into a cache table with assistance of the jcman function. These functions (jcsearch and jcman) are command-line interfaces to ChemAxon Java programs and these functions connect with MySQL via the JDBC Connector/J.

According to one aspect, a 'Query' data object holds the SMILES string for a chemical compound that is the subject of a search. A 'Segment' data object holds a sub-section (e.g., approximately 1,000 entries) of the entire database. This sub-section is the target of the chemical substructure search since running a substructure search on all entries in the database would take several orders of magnitude too long to be usable. A 'Substructure' data object holds the results of the substructure search, after being executed on the contents of 'Segment'. The results include a list of the compounds found to contain the query inside their chemical structure. Finally, each time 'Substructure' is filled, data is appended onto the end of a 'Cache' data object, which holds all search results generated for a given query. The drug informatics database carries out its search through the entire database 'incrementally' and thus the 'Segment' and 'Substructure' data stores will be repeatedly filled, examined, and deleted, as the search process incrementally works its way through the entire database.

This functionality may be performed, for example, by 'cmdline_insert_into_screening.php' which is a PHP script. In one embodiment, 'cmdline_insert_into_screening.php' clears the screening table and loads 10,000 records from the jcman_unified table into the screening table. Next, it deletes the jcsearchresults_PHPSESSIONID.sdf file and uses 'jcsearch' to apply a substructure search on the screening table. The result of this search is deposited into a /search_cache/folder as jcsearchresults_PHPSESSIONID.sdf. Finally, 'cmdline_insert_into_screening.php' uses 'imam' to write the jcsearch results file into the jcsearch table, which is a cache table from which results are read for display to the user, and updates the jcsearch table's SMILES column to remove the first blank space and all text after that in order to obtain all words after the first word.

At step 112, the search results are provided to a user. Providing the search results may include providing an initial set of search results within a first time period and providing an updated set of search results within a second time period, where the first time period is less than the second time period. For example, assuming that the total number of matches in the database is one hundred search results, initial search results constituting ten search results may be provided in ten seconds or less while the remaining search results are obtained. As the user reviews the initial search results, the remaining ninety search results may be obtained within five minutes or whatever time period is required based on the size and configuration of the database, the number of matching search results, and the complexity of the search query. Thus, in one embodiment, initial search results are retrieved after a few seconds, such as approximately seven seconds on test-servers, however it is appreciated that live servers may be significantly faster depending on number of users. While the user browses these results, further results are retrieved by the server and periodically updated to the browser without interrupting service. At any point, the user may save a copy of all search results gathered so far, in .sdf format.

It is appreciated that the search results may be periodically updated and displayed without interrupting interactability with the drug informatics database. For example, a search results page displays the current contents of the cache table and an AJAX-based pagination-bar loads small portions of those results, based on user-input. Whenever the user interacts with the pagination bar, an asynchronous request is sent to search another incremental unit of the database. The results of this search are added to the cache table without interrupting the user's ability to browse results.

Providing the search results to the user may include presenting the search results in an .sdf format. For example, the search results may be presented in two or more sortable columns, where the number and nature of the columns is user-selectable. Screenshots of exemplary web pages for receiving a search query and presenting the search results to the user are shown in FIGS. 2 and 3 and are described in greater detail below.

Figure 2:
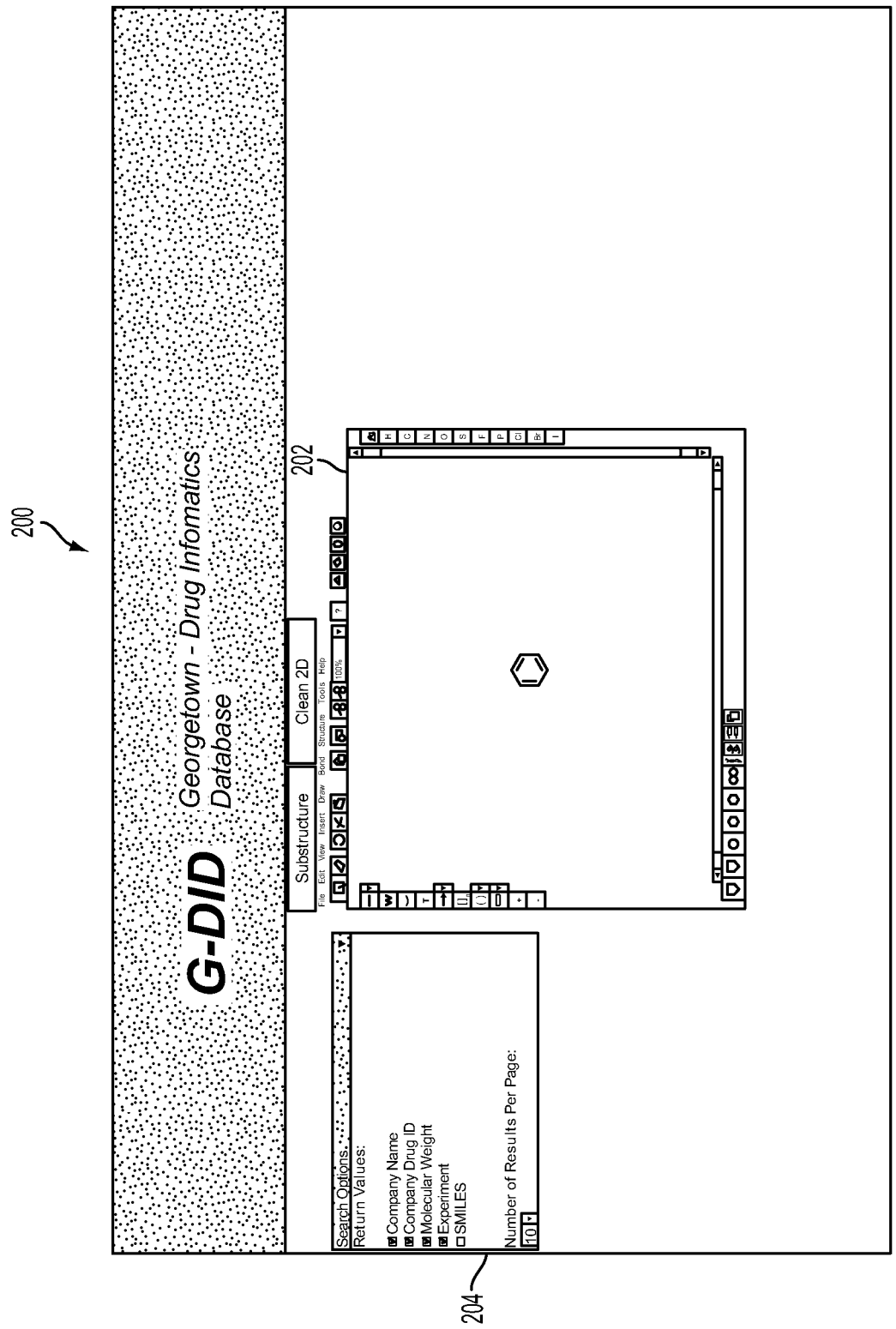
FIG. 2 is a screenshot of an exemplary search interface for searching a drug informatics database according to an embodiment of the subject matter described herein.

FIG. 2 is a screenshot of an exemplary search interface for searching a drug informatics database according to an embodiment of the subject matter described herein. Referring to FIG. 2, search interface 200 includes a search box 202 that includes space for drawing a chemical structure as the search query. For example, in order to search the drug informatics database, a user may draw a chemical compound into the search box 202. The drawn compound is converted into a SMILES string and this string, along with some auxiliary user data, is temporarily stored in the database. A search options dialog 204 allows the user to select various search options for searching the data stored in the data structures located in the drug informatics database including chemical properties and other parameters such as a number of search results per page, company name, company drug id, molecular weight, experimental data, and SMILES Thus, the user may customize the results to be returned based on chemical properties, parameters, or other data stored in the database including company name, company drug id, molecular weight, a link to experimental (bibliographic) information (if available), or the smiles string—as well as the number of results per page.

Figure 3:
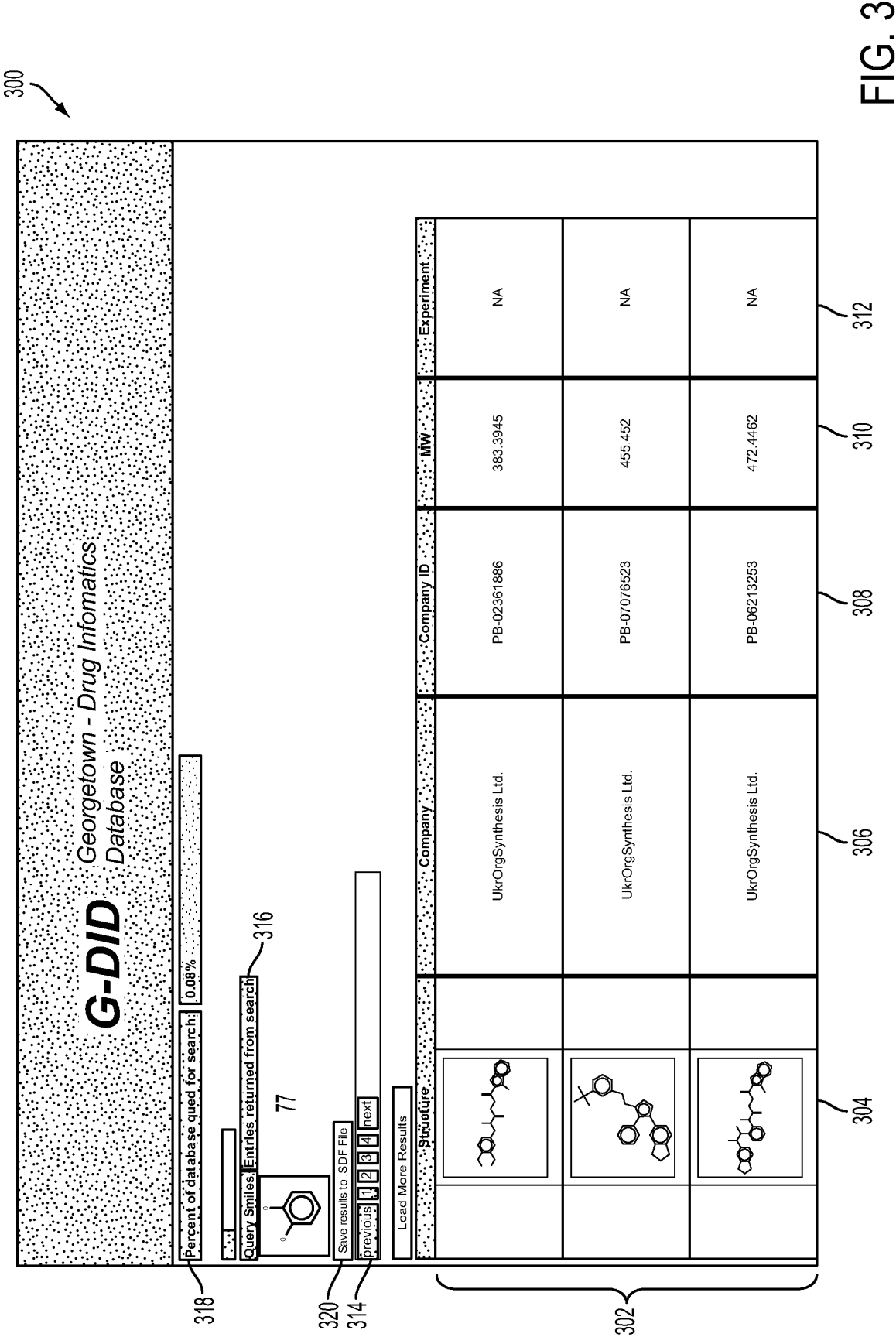
FIG. 3 is a screenshot of an exemplary search results interface for a drug informatics database according to an embodiment of the subject matter described herein. Initial search results are retrieved after a few seconds.

FIG. 3 is a screenshot of an exemplary search results interface for a drug informatics database according to an embodiment of the subject matter described herein. Initial search results are retrieved after a few seconds. While the user browses these results, further results are retrieved by the server, and periodically updated to the browser, without interrupting service. At any point, the user may save a copy of all search results gathered so far, in .sdf format. Referring to FIG. 3, search results interface 300 includes a search results screen portion 302 that includes a plurality of user-customizable columns. In the embodiment shown, column 304 displays the chemical structure, column 306 displays the company name associated with the chemical, column 308 displays the company id associated with the chemical, column 310 displays the molecular weight of the chemical, and column 312 displays or links to additional experimental or bibliographic data for the chemical.

Selection dialog 314 allows the user to select the number of search results per page that are presented in the search results interface 300. For example, in the embodiment shown, search results tally screen portion 316 indicates that seventy-seven entries are returned for the current search and search results percentage screen portion 318 indicates that 0.08% of the database is queued for search. Lastly, save dialog 320 allows the user to export or save the search results to an .sdf file or any other suitable format.

Figure 4:
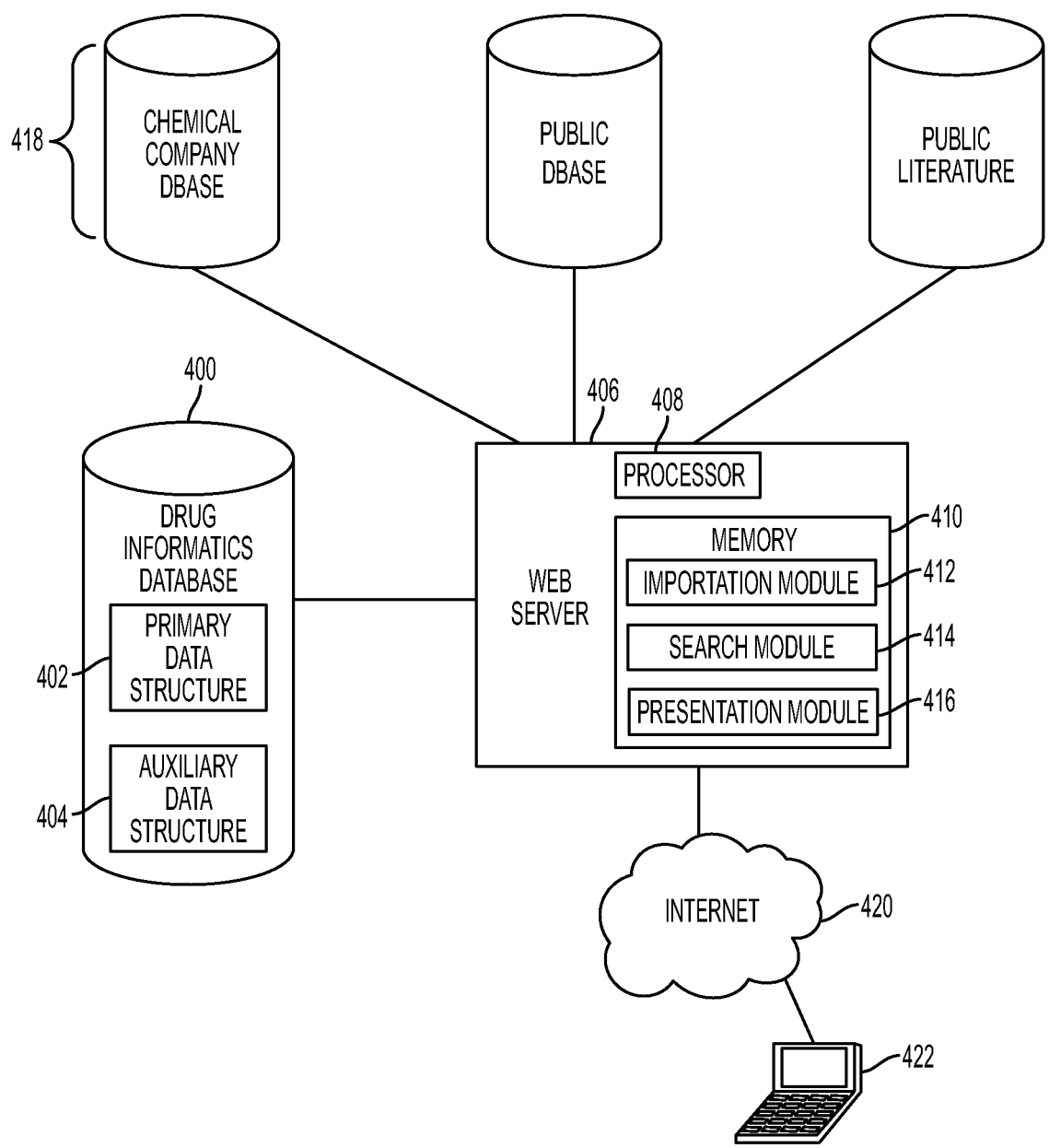
FIG. 4 is a functional block diagram of an exemplary system for populating and searching a drug informatics database according to an embodiment of the subject matter described herein.

FIG. 4 is a functional diagram of an exemplary system for populating and searching a drug informatics database according to an embodiment of the subject matter described herein. Referring to FIG. 4, the drug informatics database 400 includes a primary data structure 402 for storing primary data objects in entries, where the data structure is searchable based on one or more of the data object associated with one or more chemical compounds. Primary data structure 402 may include one or more permanent database tables which include read-only data stores shared by all-users. These tables may be referred to as permanent because a user's activity will never result in data being written or deleted from permanent tables. For example, the jcman_unified table may be a permanent primary data table, and the experiment table may be a permanent secondary data table stored in primary data structure 402.

As mentioned earlier, the primary data structure 402 stores a plurality of data objects as entries in the database 400 that are linked or associated with each other for searching. These data objects may store chemical properties and experimental data obtained from the one or more data sources 418, which are associated with one or more chemical compounds/drugs, and are stored in the database 400. Exemplary chemical and/or biological properties, including experimental and/or bibliographic data (if available), are listed in Table 1 below.

TABLE 1 acid number—The acid number is the quantity of base, expressed in terms of milligrams of potassium hydroxide, that is required to neutralize the acidic constituents in 1 g of the material.
acid/base dissociation constant (Ka/Kb)—This is used for Ka, pKa, Kb, and/or pKb values for the material.
acoustic impedance—This is used for values of the acoustic impedence of the material.
adhesive strength—This is used for values of the tensile force required to separate the material from the surface of another material.
ADME (absorption, distribution, metabolism, excretion)—This is used to indicate the presence of data relating to absorption, distribution, metabolism and excretion of an TABLE 1-continued exogenous substance (drug or xenobiotic/toxicant) in a biological (in vivo, in vitro) or a biological simulation model system (pharmacokinetics, PBPK, and/or toxicokinetics).
band gap—This is used for values of the energy difference between two allowed bands (ordinarily the highest valence band and the lowest conduction band) in the electronic structure of the material.
bending strength—This is used for values of the critical bending load that the material can withstand without failure.
Beta decay reaction energy—This is used for values of the energy released in beta decay of the material.
bioconcentration factor—This is used to indicate the presence of experimentally determined data for the steady state ratio of the concentration of the material in tissues of a fish or other organism to the concentration of the material in the surrounding water medium.
birefringence Birefringence is the formation of two unequally refracted rays when a ray of light passes through certain crystals.—This is used for values of the difference in refractive indices indicated by these two rays for the material.
boiling point—This is used for values of the temperature at which the vapor pressure of the liquid being is equal to the external pressure.
bond angle—This is used to indicate the presence of values for interatomic bond angles within the structure of the material.
bond length—This is used to indicate the presence of values for interatomic bond lengths within the structure of the material.
boron-11 NMR spectra—This is used to indicate the presence of boron-11 NMR spectra and/or spectral data for the material.
breakdown vole—This is used for values of the breakdown vole of the material. The breakdown vole is vole at which electric breakdown in a dielectric occurs.
brittle temperature—This is used for values of the temperature below which the material is brittle.
carbon-13 NMR spectra—This is used to indicate the presence of carbon-13 NMR spectra and/or spectral data for the material.
circular dichroism spectra—This is used to indicate the presence of circular dichroism spectra, including magnetic circular dichroism spectra, for the material.
cloud point Point of phase separation of a liquid system characterized by the appearance of turbidity or haziness.
complex modulus—This is used for values of the complex modulus (the ratio of stress to strain where each is a vector that may be represented by a complex number) for the material.
compressibility—This is used for values of compressibility or bulk modulus of the material.
compressive strength—This is used for values of the maximum compressive stress that the material can withstand without failure.
contact angle—This is used for values of the angle formed at the interface where a liquid droplet interacts with a solid horizontal surface at thermal equilibrium.
creep rate—This is used for values of the slope of the creep-time curve for the material.
creep strength—This is used for values of the constant stress that causes a specified quantity of creep over a given time in a specified constant environment in the material.
critical micelle concentration—This is used for values of the concentration of the material (usually a surfactant) at which the concentration of singly dispersed molecules of the material is virtually constant.
crystal lattice parameters—This is used when lattice parameters are provided for the material without full crystal structure information.
crystal structure—This is used to indicate the presence of complete crystal structure data for the material.
crystallization temperature—This is used for values of the temperature at which the material undergoes a transition from a noncrystalline to a crystalline phase.
Curie temperature—This is used for values of a transition temperature below which the substance being indexed is ferromagnetic or ferroelectric and above which it is paramagnetic and thus cannot be magnetized by an outside force and loses its residual magnetism.
Debye temperature—This is used for values of the temperature of the highest normal mode of vibration of a crystal of the material.
decay energy (Q-value)—This is used for values of the energy released in a nuclear reaction decay indicated by the difference in mass of the initial nucleus and the sum of the masses of the end products for the material.
density—This is used for values of density or specific volume of a material. Density is defined as a ratio of mass to volume for the material. Specific volume is the reciprocal of density.
dielectric constant—This is used for values of the dielectric constant of the material. The dielectric constant is an index of the ability of a dielectric to store electric charge when it is polarized in an electric field.
dielectric loss—This is used for values of the dielectric loss of the material. Dielectric loss is a measure of the power of an applied alternating current absorbed (i.e. dissipated as heat) in the dielectric.
dielectric strength—This is used for values of the dielectric strength of the material. The dielectric strength is the maximum electric field that a dielectric can withstand without physical breakdown and permanent loss of insulating properties.
diffusion coefficient—This is used for values of the diffusion coefficient of the material as it passes through another substance.
dissociation constant—This is used for values of the equilibrium constant for dissociation of the material.
ductility—This is used for values of the amount of inelastic deformation which can be produced in the material before complete failure.

TABLE 1-continued electric conductance and electric resistance Electric conductance is the ratio of the current carried through the material to the difference in the potential applied across it. Resistance is its reciprocal. Units are commonly siemans or ohm-1 for the former and ohm for the latter.
electric current-potential curve—This is used for graphical information relating to the flow of electric current in the material with respect to an applied potential.
electron affinity—This is used for values of the energy associated with the addition of an electron to the material.
electron spectra—This is used for electron energy loss spectra and for electron emission spectra.
elementary particle lifetime—This is used for values of the lifetime before decay of the particle being.
elementary particle mass—This is used for values of the mass of the particle being.
elongation at break—This is used for values of the maximum tensile strain, ofter expressed as the percene elongation, to which the material can be subjected before it breaks.
elongation at yield—This is used for values of the strain, often expressed as the percene change in length, at the yield point of the material.
emission/luminescence spectra—This is used to indicate the presence of emission spectra and emission spectral data in the UV and/or visible and/or IR and/or x-ray regions.
Enthalpy—This is used for values of enthalpy characterizing the material or for values of enthalpy changes for processes initiated by or on, and/or ending in, a single material, which is the material.
entropy—This is used for values of entropy characterizing the material or for values of entropy changes for processes initiated by or on, and/or ending in, a single material, which is the material.
ESR spectra—This is used to indicate the presence of electron spin resonance spectra and/or spectral data for the material.
Faraday effect—This is used for values of the rotation of polarization of a beam of polarized light on transmission through the material in the presence of an applied magnetic field.
fatigue strength—This is used for values of the highest stress that can be applied for a given number of cycles without fracture of the material.
fission threshold—This is used for values of the minimum (kinetic) energy of a neutron required to induce fission of the nuclei of the material.
flash point—This is used for values of the temperature at which the material will form an ignitable mixture in air.
flexural modulus—This is used for values of the ratio of stress to strain in flexure within the elastic limit of the material
fluorine-19 NMR spectra—This is used to indicate the presence of fluorine-19 NMR spectra and/or spectral data for the material.
formation enthalpy—This is used for values of the enthalpy of formation of the material.
formation entropy—This is used for values of the entropy of formation of the material.
fracture strength—This is used for values of the normal stress at the beginning of fracture of the material.
fracture toughness—This is used for values of the resistance of a material to the extension of a crack. The term fracture toughness is usually associated with the fracture mechanics methods that deal with the effect of defects on the load-bearing capacity of structural components. Fracture toughness is an empirical material property that is determined by one or more of a number of standard fracture toughness test methods.
freezing point—This is used for values of the temperature at which the material changes from a liquid to a solid.
friction coefficient—This is used for values of the ratio of the frictional force (i.e., the resistance to sliding or rolling of one solid in contact with another) to the normal force pressing surfaces together for the material.
fusion enthalpy—This is used for values of the enthalpy associated with the solid-liquid transition of the material at its melting point.
fusion entropy—This is used for values of the entropy associated with the solid-liquid transition of the material at its melting point.
gamma ray spectra—This is used to indicate the presence of gamma ray spectra and/or spectral data for the material.
Gibbs free energy—This is used for values of Gibbs free energy (free energy at constant pressure) for processes initiated by or on, and/or ending in, a single substance, which is the substance.
glass transition temperature The glass transition of an amorphous material is a reversible, second order phase transition characterized by a transition from a hard, glassy or brittle condition to a flexible fluid, or elastomeric condition. The glass transition temperature is the approximate midpoint to the temperature range over which the glass transition takes place.
glass working temperatures—This is used for values of temperatures related to the working and processing of glass.
half-life (biological)—This is used for values of the biological half-life of the material.
half-life (radionuclides)—This is used for values of the half-life (period in which one-half of an initial amount of the material is converted by radioactive decay processes into different materials and energy) of the material.
Hall effect coefficient—This is used for values of the coefficient relating to the magnitude of the transverse field developed in a conductor in a magnetic field divided by the product of the current density and magnetic induction for the material.
hardness—This is used for values of the resistance of the material (in bulk) being to penetration or deformation.
haze—This is used for values of the percene of light that is diverted by forward scattering in passing through a sample of the material.

TABLE 1-continued heat capacity—This is used for values of heat capacity (C) characterizing the material. The term "heat capacity" is defined as the quantity of heat necessary to raise the temperature of a unit mass of a substance by one degree.
Helmholtz free energy—This is used for values of Helmholtz free energy (free energy at constant volume) for processes initiated by or on, and/or ending in, a single substance which is the substance. This is not used for Helmholtz free energy of activation.
hydrodynamic radius—This is used for the value of the radius of a hypothetical hard sphere that diffuses in a viscous medium with the same velocity as a particle of the material.
ignition point—This is used for values of the minimum temperature at which the material will ignite and continue to burn in a self-sustained manner.
impact strength—This is used for values of the energy required by shock loading to fracture the material.
interfacial tension—This is used for values of the force acting to reduce the surface area of the material at an interface with a liquid or solid. When the interface is between the material and a gas or a vacuum, the "surface tension" should be used.
ionization potential—This is used for values of the energy required to remove an electron from the material in the gas phase.
IR absorption spectra—This is used to indicate the presence of IR absorption/transmission spectra and/or spectral data for the material.
IR emission/luminescence spectra—This is used to indicate the presence of IR emission spectra and/or spectral data for the material.
IR reflectance spectra—This is used to indicate the presence of IR reflectance spectra and/or spectral data for the material.
IR spectra—This is used to indicate the presence of IR absorption/transmission and/or reflectance spectra and/or spectral data for the material.
Kerr effect (magnetooptical)—This is used for values of the rotation of polarization of a beam of polarized light on reflection from the surface of the material in the presence of an applied magnetic field.
LC50 This is used to indicate presence of data for an experimentally determined median lethal concentration(s) that causes 50% mortality in organisms exposed to the material.
LD50—This is used for values of experimentally determined LOSO (lethal dose, 50%) data.
light scattering—This is used to indicate the presence of light scattering data for the material.
liquid crystal transition temperature—This is used for values of the temperature at which the material undergoes a transition from one liquid crystalline phase to another, from a liquid crystalline phase to a non-liquid crystalline phase, or from a non-liquid crystalline phase to a liquid crystalline phase.
logD—This is used for values of experimentally determined equilibrium octanol-water partition coefficients for dissociative systems (sometimes referred to as the octanol-water distribution coefficient), when the material has one or more ionizable groups.
logP—This is used for values of octanol-water partition coefficients, where the (experimentally determined) coefficient is the ratio of the concentration of the material in octanol and in water at equilibrium.
loss modulus—This is used for the imaginary part of the complex modulus for the material.
magnetic anisotropy—This is used for values of the orientation-dependent differences in the magnetic properties of the material.
magnetic coercivity—This is used for values of the strength of the magnetic field which must be applied to the material to make the magnetic induction go to zero.
magnetic domain (wall length, energy, etc.)—This is used for values of characteristics of a magnetic domain, such as the domain wall length or energy.
magnetic moment—This is used for values of the intrinsic magnetic moment (ratio of torque exerted on an atom or molecule by a magnetic field to the field strength) of the material.
magnetic susceptibility—This is used for values of the ratio of the magnetization induced in the material by an external magnetic field to the strength of the field.
magnetization—This is used for values of the magnetic moment per unit volume of the substance being producing the moment.
magnetoelastic coupling coefficient—This is used for values of the dependence of the magnetic energy density of a crystal lattice on the state of strain at a given temperature.
magnetoresistance—This is used for values of the change in the electric resistivity of the material produced by the application of a magnetic field.
magnetostrictive constant—This is used for values of the degree of expansion or contraction (change in length/initial length) of the material for a given change in magnetic flux at a specific temperature.
martensitic transition temperature—This is used for values of the temperature at which the material being undergoes a phase transition to or from a martensitic phase.
mass spectra—This is used to indicate the presence of mass spectra and/or spectral data for the material.
melt flow index—This is used for values of the amount of the material that can be forced through a selected orifice at a fixed temperature in a given time period.
melting point—This is used for values of the temperature at which the material changes from a solid to a liquid. This is also used for decomposition temperatures for solids which are encountered when attempting to measure melting point data. The decomposition temperatures are commonly reported as "mp 150-54 (dec.)" or "mp >210 C.(decompn.)" in the literature.
metal NMR spectra—This is used to indicate the presence of NMR spectra and/or spectral data of a metallic nuclei for the material.
microhardness—This is used for values of the resistance of specific microscopic regions of the material to penetration or deformation.
microwave spectra—This is used to indicate the presence of microwave absorption/transmission spectra and/or spectral data for the material.
minimum inhibitory concentration—This is used to indicate the presence of data for the lowest concentration of the material which inhibits microbial growth.

TABLE 1-continued molecular electric dipole moment—This is used for values of the intrinsic electric dipole moment of the material.
molecular structure—This is used when there is complete information about the structure of molecules of the material. s such as bond length, bond angle, etc. should be used when only partial information is provided.
molecular weight (polymers)—This is used for measured values of the molecular weight of the polymer being.
molecular weight distribution—This is used for values of the distribution of molecular weights in a polydisperse polymer, usually expressed as the ratio of weight-average molecular weight to the number average molecular weight of the polymer being.
Mossbauer spectra—This is used to indicate the presence of Mossbauer spectra and/or spectral data for the material.
neutron capture cross-section—This is used for values of the cross-section for capture of neutrons by the nucleus being.
neutron diffraction pattern—This is used to indicate the presence of a neutron diffraction pattern for the material.
neutron scattering—This is used to indicate the presence of neutron scattering data for the material.
neutron-induced fission cross-section—This is used for cross-section values for neutron-induced fission of the nuclei of the material.
nitrogen-15 NMR spectra—This is used to indicate the presence of nitrogen-15 NMR spectra and/or spectral data for the material.
NMR solution structure (complete)—This is used to indicate the presence of complete NMR solution structure data for the molecules (large molecules such as peptides, proteins, or nucleic acids) being.
NMR spectra—This is used to indicate the presence of NMR spectra and/or spectral data for the material.
NOAEL|LOAEL—This is used to indicate presence of experimentally determined data for the lowest-observed (LOAEL) and/or no-observed effects (NOAEL) levels (adverse or not) for the material.
nonlinear optical susceptibility—This is used for values of the nonlinear optical susceptibility coefficients of the material.
nuclear binding energy—This is used for values of the energy associated with (usually released in) the formation of a nucleus of the atoms of material from subnuclear particles (e.g., neutrons, protons, etc.).
nuclear energy level—This is used for values of the energy difference between the nuclear ground state and an exited level of the nucleus being.
nuclear magnetic moment—This is used for values of the intrinsic magnetic dipole moment of the atomic nucleus of the material.
nuclear transition probability—This is used for values of the probability of a transition from one nuclear level to another level in the nucleus to be.
optical rotation—This is used for molar, specific, and observed values of the amount by which polarized light is rotated by the material.
optical rotatory power Degree of rotation to the left (−) or right (+) of the plane of polarization
of a beam of light upon passing through a molecule containing one or more asymmetric carbon atoms.
organic carbon sorption coefficient—This is used for values of organic carbon-water partition coefficients, where the (experimentally determined) coefficient is the ratio of the concentration of the material sorbed per unit mass of organic carbon to the concentration in solution at equilibrium.
P-wave velocity—This is used for values of the velocity of the compressional (P) wave in the material in a geological system.
particle size—This is used for reported values of the size or size distribution of particles of the material.
partition coefficient—This is used for values associated with the equilibrium concentrations of the material in two phases, excluding values obtained for in vivo systems.
permeability—This is used for values of the rate of passage of a liquid or gas through the material under specified conditions.
phase diagram—This is used to indicate the presence of a phase diagram including the material.
phosphorus-31 NMR spectra—This is used to indicate the presence of phosphorus-31 NMR spectra and/or spectral data for the material.
photoelectron spectra—This is used to indicate the presence of photoelectron spectra and/or spectral data for the material.
piezoelectric coefficient—This is used for values of the coefficient relating the compressional stress in any direction to the resulting dielectric polarization in the same direction for the material.
Poisson ratio—This is used for values of the Poisson ratio of the material.
pore size—This is used for reported values of the size or size distribution of pores in the material.
porosity—This is used for values for the ratio or percene of the volume of voids or interstices in the material to its total volume. This includes the total volume of both closed and open pores.
potential of electrode reaction—This is used for values of the potential for reduction or oxidation of the material at an electrode under the given experimental conditions.
proton NMR spectra—This is used to indicate the presence of proton NMR spectra and/or spectral data for the material.

TABLE 1-continued radiation attenuation/transmission coefficient There is no description available at this time
radius of gyration—This is used for the value of the average squared distance of all points within a particle to the center of gravity of that particle of the material.
Raman spectra—This is used to indicate the presence of Raman spectral data for the material.
reactivity ratio in polymerization This is applied for the value of relative likelihood for a monomer radical at a growing polymer chain end to be attacked either by another molecule of the same monomer (i.e., the material) or by a molecule of a second, different monomer.
refractive index—This is used for values of the ratio of the velocity of light in vacuum to the velocity of light in the material.
remanence—This is used for values of the magnetization remaining on changing the magnetic field to zero for the material.
residual stress—This is used for values of tension or compression which exist in the bulk of a material without application of an external load.
S-wave velocity—This is used for values of the velocity of the shear (S) wave in the material in a geological system.
saponification number—This is used for values of the quantity of potassium hydroxide required to saponify a fixed quantity of the material.
shear modulus—This is used for values of the shearing modulus (the ratio of the applied shear stress to the resulting strain) of a material undergoing shear deformation.
shear strength—This is used for values of the maximum shear stress that can be sustained before structural failure of the material.
silicon-29 NMR spectra—This is used to indicate the presence of silicon-29 NMR spectra and/or spectral data for the material.
softening point—This is used for values of the temperature at which the material goes from rigid to soft (plastically deformable).
solubility This is used for values of the amount of the material that can be dissolved in a selected solvent system.
sound attenuation coefficient—This is used for values of the decrease in sound wave energy per unit distance traveled through the material.
sound velocity—This is used for values of velocity at which sound waves propagate through the material.
specific surface area—This is used for values for the specific surface area (surface area/unit mass or surface area/unit volume) of the material.
storage modulus—This is used for the real part of the complex modulus for the material.
sublimation temperature—This is used for values of the temperature at which a substance passes from the solid phase to the gaseous phase (or from the gaseous phase to the solid phase) without passing through a liquid phase.
superconductivity—This is used for values of temperatures, electric currents, and/or magnetic fields related to the onset or destruction of zero-resistance behavior in superconductive materials being.
surface tension—This is used for values of the force acting to reduce the surface area of the material at an interface with a gas or vacuum.
tear strength—This is used for values of the force required to propagate a tear in the material.
tensile strength—This is used for values of tensile strength, broadly defined as stress or force/original cross sectional area corresponding to a given strain of the material being tested. This includes reported values of tensile strength at yield, at break or highest (ultimate) stress.
thermal analysis—This is used to indicate the presence of data from thermal analysis techniques, which characterize the thermal relaxations, phase transitions and decomposition of the material over a specified range of temperatures.
thermal conductivity—This is used for values of the thermal conductivity of the material. The thermal conductivity of a material is the heat transfer through the material across a temperature gradient which is not associated with macroscopic displacements in the material. The thermal conductivity is defined as the heat flow per unit time, per unit temperature gradient across a unit cross-sectional area.
thermal expansion coefficient—This is used for values of the ratio of an expanded length or volume to an original length or volume resulting from increasing the temperature of the material by one unit of temperature from a specified temperature (generally in units of 1 fT at a specified temperature).
thermal fatigue—This is used for values of the result of rapid thermal cycling, causing nonuniform dimensional changes leading to distortion or fracture of the material.
toxic equivalence factors—This is used to indicate presence of data for experimentally based relative potency factors such as the ratio of toxicity measures for a reference compound (e.g. the LOAEL of TCDD) to the toxicity of an index congener (e.g. the LOAEL of another dioxin congener).
triple point—This is used for values of the temperature and pressure at which the solid, liquid, and vapor phases of the material are in equilibrium.
two-dimensional NMR spectra—This is used to indicate the presence of two-dimensional NMR correlation spectra and/or spectral data for the material.
UV and visible absorption spectra—This is used to indicate the presence of UV and/or visible absorption/transmission spectra and/or spectral data for the material.
UV and visible emission/luminescence spectra—This is used to indicate the presence of UV and/or visible emission spectra and/or spectral data for the material.
UV and visible reflectance spectra—This is used to indicate the presence of UV and/or visible reflectance spectra and/or spectral data for the material.
UV and visible spectra—This is used to indicate the presence of UV and/or visible absorption/transmission and/or reflectance spectra and/or spectral data for the material.
vapor pressure/volatility—This is used for values of the equilibrium vapor pressure or volatility of the material.

TABLE 1-continued viscosity Viscosity is a measure of a fluid's resistance to flow.—This is used for the ratio between the shear stress and the velocity gradient or rate of shear for the material.
water sorption capacity—This is used for values describing the ability of the material to sorb water.
wear rate—This is used for values of the rate at which material is lost from the surface of the material due to wear.
x-ray absorption spectra—This is used to indicate the presence of x-ray absorption/transmission spectra and/or spectral data for the material.
x-ray diffraction pattern—This is used to indicate the presence of an x-ray diffraction pattern for the material.
x-ray emission/luminescence spectra—This is used to indicate the presence of x-ray emission spectra and/or spectral data for the material.
x-ray reflectance spectra—This is used to indicate the presence of x-ray reflectance spectra and/or spectral data for the material.
x-ray scattering—This is used to indicate the presence of x-ray scattering data for the material.
x-ray spectra—This is used to indicate the presence of x-ray spectral information for the material.
Young's modulus—This is used for values of the Young's modulus (ratio of applied tension stress to resulting strain parallel to the tension) for the material.

An auxiliary data structure 404 within the drug informatics database 400 stores auxiliary data objects in entries associated with the one or more chemical compounds, where the auxiliary data objects are linked to the primary data objects. Auxiliary data structure 404 may include one or more temporary database tables which are created whenever a user starts a new search and are deleted when a new search is begun, or after a short period of inactivity (e.g., fifteen minutes). These temporary tables are user specific and may be named based on the user's PHP Session ID. The query, screening, and jsearch tables may be temporary tables stored in auxiliary data structure 404. For example, the query table may be a very small temporary table that holds queries for use by jchem functions, the screening table may be a temporary table which is used to hold a subset of the jcman_unified table to operate on, and the jcsearch table may be a cache table which holds all cumulative results of the search.

The drug informatics database 400 may also be connected to a web server 406 for providing various functionality associated with transmitting or receiving information from one or more external online sources. For example, the database 400 may be integrated with, co-located with, or remotely connected the web server 400 via any suitable communications link. The web server 406 may include a processor 408 for executing non-transitory computer readable instructions stored in a computer readable medium, such as memory 410. The memory 410 may include a plurality of software modules for providing the functionality described herein.

An importation module 412 may be configured to import data obtained from one or more data sources by converting or processing the data into a format required or understood by the drug informatics database 400. For example, the importation module 412 may be configured to receive unprocessed data associated with a chemical compound from the data sources 418, parse the unprocessed data into a plurality of data objects based on a categorization associated with each of the data objects, and identify and associate additional information, such as explanatory notes, with the data objects. The importation module 412 then stores the data objects as searchable entries in the drug informatics database 400.

A search module 414 may be configured to receive a query for data associated with a chemical compound and search the drug informatics database 400 for data associated with the chemical compound. For example, the search module 414 may receive a query in the form of a visual representation of a chemical compound and convert the visual query into a search string that is understandable by the database. Other search functions provided by the search module 414 may include using one of structure-based searching, property-based searching, similarity-based searching, or matching similarity over existing experimentally validated compounds.

A presentation module 416 may be configured to provide the search results to the user. In one embodiment, the presentation module 416 consists of a number of PHP scripts, which dynamically generate HTML and CSS pages, using AJAX methods (e.g., via Javascript and the pervasive Javascript library jQuery). This provides a web-based interface to the extensive MySQL database of chemical compounds 400 relevant for inquiry-based exploratory cheminformatics.

The web server 406 may be connected to a plurality of data sources 418 containing information associated with chemical compounds. For example, data sources 418 may include chemical company databases, public databases, and public literature. Unprocessed information from these data sources 418 may be received and processed by the importation module 412 and the processed data may be stored in the drug informatics database 400.

The primary data structure stores primary data objects in entries, where the data structure is searchable based on one or more of the data object associated with one or more chemical compounds. In one exemplary embodiment, we begin with each compound represented by its chemical structure in the format of an MDL Molfile. Associated auxiliary data is included, if available, and the MDL Molfile may be converted to an SDF file. These data are then imported into the database. For example, this may include importing into an MySQL database via ChemAxon's JChemManager function. This process automatically generates several additional data fields, including SMILES and molecular weight.

Several additional fields are used by the drug informatics database 400, including one or more companies supplying the compound, the company's chemical id used to identify the company, SMILES string, and a dataset tag used to identify related groups of data. For example, the dataset tag used to identify related groups of data usually refers to a set of data which was gathered at the same time.

The auxiliary data structure stores auxiliary data objects in entries associated with the one or more chemical compounds, where the auxiliary data objects are linked to the primary data objects. For compounds which have been the subject of experimental inquiry, this information is gathered and used to form the auxiliary database 404. Search results may be matched against this auxiliary database 404 by comparing SMILES strings, which have been standardized as described above. If a match is found, the drug informatics database 400 provides a website link to the experimental information on the website from which the experimental information was originally drawn.

Additionally, in one possible embodiment, the drug informatics database 400 may maintain both long-term data stores and short-term data stores in order to further optimize the populating, storage, and/or retrieval of data from the drug informatics database. For example, the drug informatics database 400 may maintain two long-term stores of data. The first long-term data store is a table of chemical compounds along with associated information, such as company of origin. The second long-term data store contains information to provide a web-link to external websites which provide bibliographic information on prior studies concerning a given compound. Both of these long term data stores are wholly visible to all users which access the website. Further, both of these databases may be set to be effectively 'Read-Only', and consequently cannot be changed by any action through the website.

The drug informatics database 400 may also maintain four short-term data stores, where two of the short term data stores include files and two of the short term data stores include relational database tables. Each of these temporary data stores is user-specific, and are read from and written to in the course of a single web-based search.

While a particular embodiment has been chosen to illustrate the invention, it will be understood by those skilled in the art that various changes and modifications can be made therein without departing from the scope of the invention as defined in the appended claims.

What is claimed is:

1. A method for searching a drug informatics database, comprising:
   receiving, at a drug informatics database, a query for data associated with a chemical compound, said query in the form of a visual representation of the molecular structure of said chemical compound;
   searching the drug informatics database for data associated with the chemical compound, wherein the searching of the drug informatics database results in the deletion and recreation of query tables; and
   providing the search results to a user, wherein the search results are retrieved from a cache table and displayed using a pagination bar, wherein user interaction with the pagination bar initiates an asynchronous search of an incremental unit of the drug informatics database, and wherein the search results are browsable during the asynchronous search.

2. The method or claim 1 wherein receiving a query includes receiving a query that includes a visual representation of the chemical compound.

3. The method or claim 1 wherein searching the drug informatics database includes converting the visual representation of the chemical compound into a search string.

4. The method of claim 1 wherein searching the drug informatics database includes performing a search on a subset or the drug informatics database.

5. The method of claim 1 wherein searching the drug informatics database includes incrementally caching the search results in real time or near real time.

6. The method of claim 1 wherein searching the drug informatics database includes using one of structure-based searching, property based searching, similarity-based searching, or matching similarity over existing experimentally validated compounds.

7. The method of claim 1 wherein searching the drug informatics database includes performing a substructure search by identifying chemical compounds that contain the queried chemical structure as a substructure.

8. The method of claim 1 wherein providing the search results includes providing an initial set of search results within a first time period and providing an updated set of search results within a second time period, where the first time period is less than the second time period.

9. The method of claim 8 wherein the search results are periodically updated and displayed without interrupting interactability with the drug informatics database.

10. The method of claim 1 wherein providing the search results includes presenting the search results in an .sdf format.

11. The method of claim 1 wherein providing the search results includes presenting the search results in two or more sortable columns, where the number and nature of the columns is user-selectable.

12. A drug informatics database, comprising:
   a non-transitory computer-readable medium;
   a primary data structure on said medium for storing primary data objects in entries, where the data structure is searchable based on one or more of the data objects associated with one or more chemical compounds;
   an auxiliary data structure on said medium for storing auxiliary data objects in entries associated with the one or more chemical compounds, where the auxiliary data objects are linked to the primary data objects; and
   wherein the drug informatics database maintains both long-term data stores and short-term data stores in order to optimize population, storage, and/or retrieval of data objects, and wherein said drug informatics database accepts searches in the form of a visual representation of a chemical molecular structure of the one or more chemical compounds, wherein the results of searches are retrieved from a cache table and displayed using a pagination bar, wherein interaction with the pagination bar initiates an asynchronous search of an incremental unit of the drug informatics database, and wherein the search results are browsable during the asynchronous search.

13. The database of claim 12 wherein the primary data structure includes a dataset tag used to identify related groups of data.

14. The database of claim 12 further comprising a web server including:
   a computer-readable medium for storing non-transitory computer readable instructions;
   a processor for executing the non-transitory computer readable instructions stored in the computer-readable medium, where the computer-readable medium includes:
      an importation module for:
         receiving unprocessed data associated with a chemical compound from one or more data sources;
         parsing the unprocessed data into a plurality of data objects based on a categorization associated with each of the data objects;

identifying and associating additional information including explanatory notes with at least one or the data objects; and storing the data objects in entries within a data structure in the drug informatics database, where the data structure is searchable based on one or more of the data objects;

a search module for receiving a query for data associated with a chemical compound and searching the drug informatics database for data associated with the chemical compound; and a presentation module for providing the search results to a user.

15. The database of claim 12 wherein the one or more data sources include one of private chemical company databases, public databases, and public literature.

* * * * *